United States Patent
Vinyard et al.

(10) Patent No.: US 12,280,164 B2
(45) Date of Patent: Apr. 22, 2025

(54) FLASHLAMP CARTRIDGE FOR DECONTAMINATION AND DECONTAMINATION UNIT

(71) Applicant: Heraeus Noblelight Ltd., Cambridge (GB)

(72) Inventors: Tony Vinyard, Cambridge (GB); Harry Shirling-Rooke, Cambridge (GB); Jeremy Woffendin, Cambridge (GB)

(73) Assignee: Excelitas Noblelight Ltd., Cambridge (GB)

( * ) Notice: Subject to any disclaimer, the term of this patent is extended or adjusted under 35 U.S.C. 154(b) by 784 days.

(21) Appl. No.: 17/424,073

(22) PCT Filed: Jan. 20, 2020

(86) PCT No.: PCT/EP2020/051219
§ 371 (c)(1),
(2) Date: Jul. 19, 2021

(87) PCT Pub. No.: WO2020/152073
PCT Pub. Date: Jul. 30, 2020

(65) Prior Publication Data
US 2022/0096679 A1    Mar. 31, 2022

(30) Foreign Application Priority Data
Jan. 21, 2019   (EP) .................................. 19152768

(51) Int. Cl.
| | | |
|---|---|---|
| G01N 21/00 | (2006.01) | |
| A23L 3/28 | (2006.01) | |
| A61L 2/00 | (2006.01) | |
| A61L 2/10 | (2006.01) | |
| G01N 23/00 | (2006.01) | |

(52) U.S. Cl.
CPC .................................... A61L 2/10 (2013.01); A23L 3/28 (2013.01); A61L 2202/11 (2013.01); A61L 2202/14 (2013.01); A61L 2202/23 (2013.01)

(58) Field of Classification Search
CPC . A61L 2/08; A61L 2/24; A61L 2/0047; A61L 2/10; A23L 3/28; C02F 1/325
USPC ...... 422/24, 32; 250/454.11, 453.11, 455.11, 250/492
See application file for complete search history.

(56) References Cited

U.S. PATENT DOCUMENTS

| | | |
|---|---|---|
| 4,910,942 A | 3/1990 | Dunn et al. |
| 5,768,853 A | 6/1998 | Bushnell et al. |

(Continued)

FOREIGN PATENT DOCUMENTS

| | | |
|---|---|---|
| DE | 102014110679 A1 | 9/2015 |
| EP | 2805912 | 11/2014 |

(Continued)

OTHER PUBLICATIONS

International Search Report and Written Opinion dated Feb. 10, 2020 for corresponding International Patent Application No. PCT/EP2020/051219.

*Primary Examiner* — Monzer R Chorbaji
(74) *Attorney, Agent, or Firm* — Wolf, Greenfield & Sacks, P.C.

(57) ABSTRACT

A flashlamp cartridge for a decontamination unit. The cartridge includes a flashtube for pulsed emissions of ultraviolet light and a sheath encapsulating the flashtube.

19 Claims, 5 Drawing Sheets

(56) References Cited

U.S. PATENT DOCUMENTS

| | | |
|---|---|---|
| 5,900,211 A | 5/1999 | Dunn et al. |
| 8,376,573 B2 | 2/2013 | Mehlmann et al. |
| 9,809,435 B2 | 11/2017 | Houde |
| 2005/0252866 A1 | 11/2005 | Beckinghausen |
| 2010/0078574 A1 | 4/2010 | Cooper et al. |
| 2016/0193775 A1 | 7/2016 | Lewin et al. |
| 2019/0091356 A1 | 3/2019 | Riedel et al. |
| 2019/0135658 A1 | 5/2019 | Yamakoshi |

FOREIGN PATENT DOCUMENTS

| | | | |
|---|---|---|---|
| JP | H11514277 A | 12/1999 | |
| JP | 2003534100 A | 11/2003 | |
| JP | 2009501039 A | 1/2009 | |
| WO | 2001091810 | 12/2001 | |
| WO | 2017157550 | 9/2017 | |
| WO | 2017208810 | 12/2017 | |
| WO | 2020152073 | 7/2020 | |
| WO | WO 01/91810 A1 * | 12/2021 | ............... A61L 2/08 |

* cited by examiner

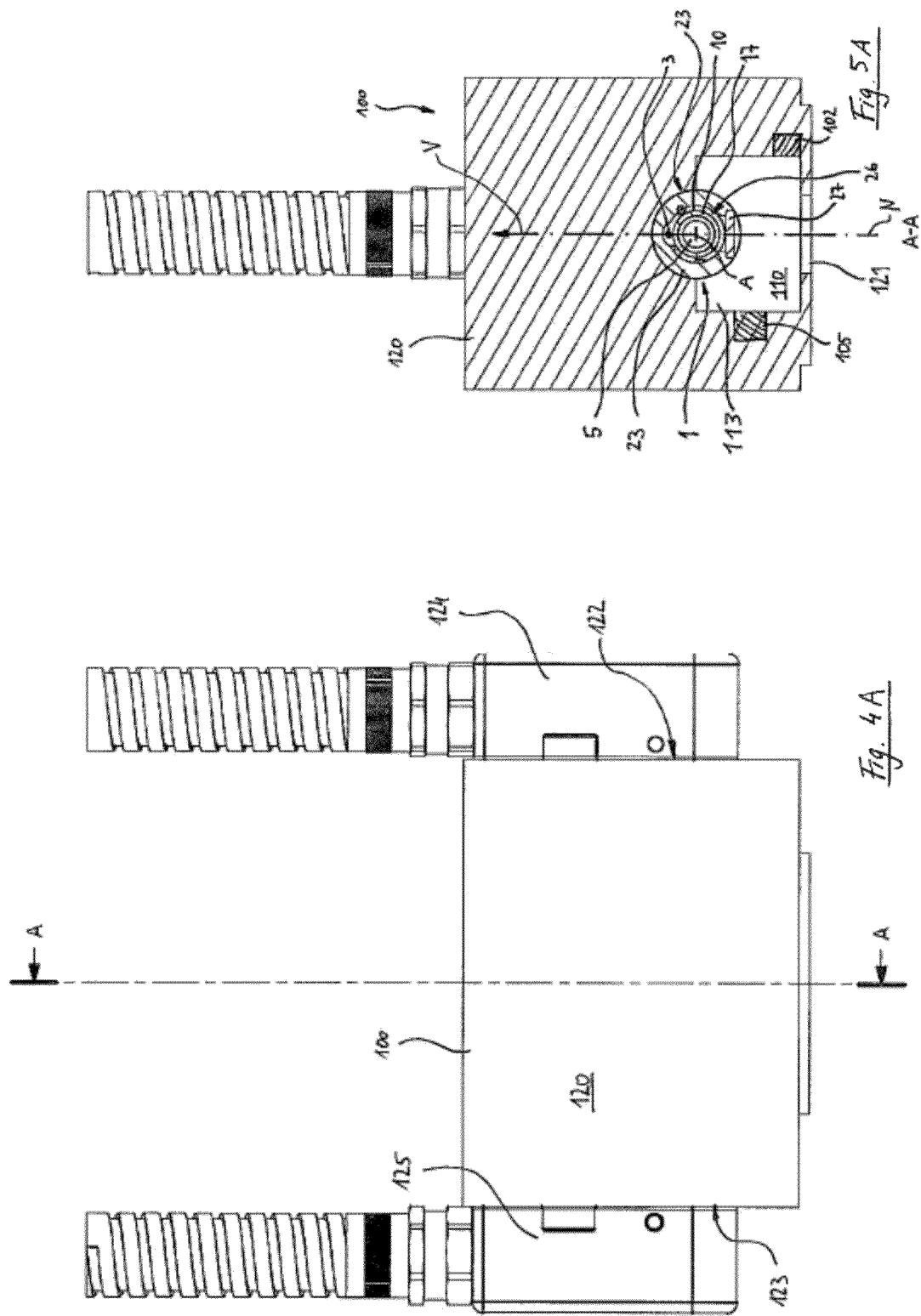

FLASHLAMP CARTRIDGE FOR DECONTAMINATION AND DECONTAMINATION UNIT

CROSS REFERENCE TO RELATED APPLICATIONS

This application is a U.S. national phase filing of International Patent Application Number PCT/EP2020/051219 filed on Jan. 20, 2020, which claims priority to European Patent Application Number 19152768 filed on Jan. 21, 2019. The disclosures of these applications are hereby incorporated by reference in their entirety.

TECHNICAL FIELD

The present invention relates to a flashlamp cartridge for decontamination comprising a flashtube for pulsed emissions of ultraviolet light. The invention also relates to a decontamination unit comprising a flashlamp for pulsed emissions of ultraviolet light.

The field of the invention is the decontamination of targets such as containers or parts thereof for packaging in the food and drug industries.

BACKGROUND OF THE INVENTION

Dry decontamination by ultraviolet (UV) radiation is in particular used in the food industry for the decontamination of containers for food products, such as bottles and cans, in particular prior to filling of the containers. The decontamination improves the preservation of the packaged products. Containers and/or food products, including beverages or dairy, are exposed to UV radiation in the production line to destroy to a desired extent or level of decontamination the microorganisms on their surfaces.

The decontamination of containers by application of UV radiation is a well-known technique, widely used in the food and medical industry. The technique exploits the ability of UV radiation to destroy cells and microorganisms due to a photochemical effect and a photothermal effect.

The photochemical effect results from the absorption of UV radiation by microorganisms. It causes breaches and formation of abnormal bonds in the DNA molecules which prevent proper DNA replication. The microorganism's protein production or cell metabolism is blocked and the microorganism dies.

The photothermal effect is obtained with pulsed UV radiation and results from the delivery to the microorganism of a high energy in a very short time. The radiation absorbed by the microorganism causes a steep increase in the internal temperature and breaches the cell's membrane.

The decontaminating efficiency of pulsed UV light has been demonstrated on a wide range of microorganisms: bacteria, mold, viruses, etc. The portion of UV radiation (in the range between 200 and 300 nm) included in the pulse results in the destruction of microorganisms present in the product subjected to the treatment. The photochemical effect has an absorption maximum of about 200 nm and 247 nm, respectively. Other ranges seen as particularly efficient for decontamination have a maximum of about 220 nm or 265 nm.

Light pulses may be generated by flashlamps. Commonly used are for example Xenon flashlamps. Flashlamps are operating in a pulsed mode. The electrical energy is accumulated in an electrical capacitor. A high-voltage (several tens of kV) signal triggers arcing in the gas contained in the lamp. The release of electrical energy produces a light emission through gas ionization. Xenon is a very efficient inert gas for converting electrical energy into light energy, in particular in the UV range. Other noble gases can also be used. The gas pressure used (equal to or higher than one bar) provides that the spectrum of flashes is continuous. The spectrum consists of the wavelength from UV to near-infrared (200 nm to 1,100 nm).

The decontamination level obtained is dependent on the number of and the power of applied flashes, and the nature of the treated surface, and ranges from a mere logarithmic reduction (destruction of a fraction of microorganisms) to full sterilization (almost complete destruction of microorganisms).

Examples of the use of pulsed ultraviolet radiation for decontamination in the food processing and pharmaceutical industry are given in U.S. Pat. No. 4,910,942 A. Different systems for decontamination using pulsed ultraviolet radiation are described in EP 2 805 912 B1; U.S. Pat. No. 9,809,435 B2; US 2016/0193775 A1 and WO 2017/157550 A1.

These systems suffer from several disadvantages, particularly when intended to be applied for industrial-scale applications in the foodstuff or pharmaceutical industry. Common flashlamps have a relatively complex design which makes their maintenance, assembly and repair cumbersome and very time-consuming. A major challenge is to guarantee a decontaminating efficiency during the entire extended lifespan of a flashlamp. To ensure this, in most applications, flashlamps are replaced at predetermined intervals leaving significant safety precautions. (By "predetermined" is meant determined beforehand, so that the predetermined characteristic must be determined, i.e., chosen or at least known, in advance of some event.) Further, in order to extend the lifespan, significant efforts are undertaken to cool the flashlamp using coolant fluids, mostly deionized water. Water-cooled systems such as the system described in U.S. Pat. No. 9,809,435 B2, however, are rather large and therefore unable to fit into tight spatial restraints. Further, the required cooling fluid circuits pose additional safety and failure risks and increase the system's overall complexity, making it even more complicated to assemble, install and repair.

For production plants used for high production volumes, it is desired to use a reliable, simple and efficient decontamination tool to ensure a continuous production workflow. If one decontamination device within a foodstuff processing plant does not work properly, the products affected by the defective tool have to be discarded for health and safety regulation reasons, or the entire production line has to be interrupted for the replacement of the decontamination tool.

In some production facilities, so-called "wet" decontamination devices are used, as these are generally relatively small and simple to maintain. Wet decontamination tools apply a flowable decontamination medium, such as hydrogen peroxide or peracetic acid, onto surfaces of foodstuff containers. One such system is described in U.S. Pat. No. 9,339,573 B2. However, the flowable decontamination mediums are highly toxic and therefore problematic when processing foodstuff as well as under general environmental, health and safety considerations.

It is generally an object of the present invention to at least partially overcome a disadvantage of the prior art.

It is a further object of the invention to provide a tool for dry decontamination dispensing with the use of toxic decontamination fluids. It is in further object of the invention to provide a decontamination tool that is easy to maintain, assemble, install, uninstall, disassemble, and/or repair. It is a further object of the invention to provide a decontamination tool that is easily employed in a high-scale industrial production facility. It is another object of the invention to provide a decontamination tool dispensing with the need for a coolant fluid. It is yet a further object of the invention to provide a decontamination tool that can easily be handled even by unskilled personnel. It is a further object of the invention to provide a decontamination tool that minimizes the environmental, health and safety risk for at least one and preferably both of the consumer of the product treated by the decontamination tool and the operators handling the decontamination tool. It is a further object of the invention to provide a particularly reliable decontamination tool able to act for a prolonged and extended lifespan. It is a further object of the invention to provide a decontamination tool of small dimensions to be able to fit within restricted spatial confinements. It is a further object of the invention to provide for a decontamination tool enabling large production volumes in a foodstuff processing plant. It is a further object of the invention to provide a decontamination tool capable of reliably delivering a required dosage over a predetermined and extended lifespan of the tool. It is a further object of the invention to effectively and reliably decontaminate a target, in particular a flat target area. It is a further object of the invention to decontaminate a target, in particular a flat target area, at a logarithmic reduction level of at least 2 (log 2) or at least 3 (log 3) or at least 4 (log 4).

It is a further object of the invention to provide a decontamination tool suitable to work in a non-sterile environment.

It is further an object of the invention to provide a decontamination unit as a decontamination tool. It is further an object of the invention to provide a flashlamp cartridge for use as a decontamination tool. It is further an object of the invention to provide a decontamination array for a large-scale production facility using multiple decontamination units.

A contribution to the at least partial fulfillment of at least one, preferably multiple of the above objects of the invention is accomplished by the disclosed subject matter.

SUMMARY OF THE DISCLOSURE

In an embodiment 1 according to the invention, a flashlamp cartridge for a decontamination unit comprises a flashtube for pulsed emissions of ultraviolet light and a sheath encapsulating the flashtube. A decontamination unit in which the flashlamp cartridge according to the invention may be used to decontaminate any target substrate including foodstuff, foodstuff containers and/or components of foodstuff containers, such as a container body or a container closure. Container bodies may include a can body, a bottle body, a bottle preform, a cup, a plate, or the like. Container closures may include a lid, including a can lid, a cap, including a bottle cap, or the like. Decontamination may include a mere logarithmic reduction (destruction of a fraction of microorganisms) or full sterilization (almost complete destruction of microorganisms). In particular, decontamination may refer to a logarithmic reduction level of at least 2 (log 2) or at least 3 (log 3) or at least 4 (log 4). According to an aspect of the invention, the flashlamp cartridge comprises a sheath and a flashtube arranged within the sheath. The flashlamp cartridge may consist of the sheath and the flashtube arranged therein. The sheath realizes a barrier between the flashtube and its environment. The sheath shields the flashtube from the environment. The sheath permits only predefined access of environmental media including electricity and gas, to and from the flashtube.

In an embodiment 2 according to the invention, wherein the flashlamp cartridge is embodied in accordance with embodiment 1, the sheath comprises at least one port comprising one or more media connectors extending through the sheath for supplying the flashtube. In particular, the sheath comprises exactly one port or exactly two ports. The port or ports of the sheath may be the exclusive gateway for environmental media to and from the flashtube.

In an embodiment 3 according to the invention, wherein the flashlamp cartridge is embodied in accordance with embodiment 2, two ports are provided on different sides of the flashlamp cartridge. By providing ports at exactly two sides or more sides of the flashlamp, the cross section of the port(s) and consequently the flashlamp cartridge may be limited so that the cartridge may fit into tight spatial restraints.

In an embodiment 4 according to the invention, wherein the flashlamp cartridge is embodied in accordance with embodiment 3, the two ports are arranged on opposite ends of the flashlamp cartridge. The cartridge may define an axial direction aligned with the extension from the first to the second opposite end. The ports may be coaxially disposed with respect to one another.

In an embodiment 5 according to the invention, wherein the flashlamp cartridge is embodied in accordance with one of the embodiments 2 to 4, exactly two ports are provided.

In an embodiment 6 according to the invention, wherein the flashlamp cartridge is embodied in accordance with one of the embodiments 2 to 5, at least one port comprises at least one of the following media connectors: (i) an electrode connector, (ii) a trigger connector, (iii) a ground connector, and (iv) a coolant connector. The at least one media connector may extend in the axial direction of the cartridge. The electrode connector may be arranged centrally in an area defined by a port. In a flashlamp having ports on opposite ends of the cartridge, the electrode connectors on the opposing ports may be arranged coaxial with one another, in particular concentrically aligned. One or more media connectors may be arranged radially offset relative to the electrode connector in the same port. The one or more media connectors may be arranged parallel relative to the electrode connector. Several media connectors may be arranged circumferentially surrounding the electrode connector. The several media connectors may be arranged concentrically with respect to the electrode connector.

In an embodiment 7 according to the invention, wherein the flashlamp cartridge is embodied in accordance with embodiment 6, exactly one port comprises the trigger connector.

In an embodiment 8 according to the invention, wherein the flashlamp cartridge is embodied in accordance with embodiment 6 or 7, a first port comprises a first electrode connector and a first ground connector and a protruding isolator arranged between the first electrode connector and the first ground connector. Particularly, in a cartridge a second port may comprise a second electrode connector and a second ground connector and a second protruding isolator arranged between the second electrode connector and the second ground connector. The first and/or optionally the second protruding isolator may extend in the axial direction at least as far as the shorter one of the respective electrode connector or ground connector.

In an embodiment 9 according to the invention, wherein the flashlamp cartridge is embodied in accordance with one of the embodiments 6 to 8, a first coolant connector and a second coolant connector are provided, wherein the first and second coolant connectors are in fluid communication such that the first coolant connector forms a coolant inlet and the second coolant connector forms a coolant outlet.

In an embodiment 10 according to the invention, wherein the flashlamp cartridge is embodied in accordance with one of the preceding embodiments, the sheath comprises an at least partially cylindrical tubular body surrounding the flashtube. The tubular body may be made of an electric isolator. The tubular body may comprise or consist of a sterilizable material. The tubular body may comprise or consist of a UV-resistant material. The tubular body may comprise or consist of an opaque material. The tubular body may concentrically surround the flashtube. The tubular body may be coaxially aligned with the flashtube. The tubular body may be coaxially aligned with at least one media connector, in particular at least one electrode connector, preferably two electrode connectors. The tubular body may comprise or consist of a metal, in particular stainless steel or aluminum, and be electrically connected to at least one ground connector of the cartridge.

In an embodiment 11 according to the invention, wherein the flashlamp cartridge is embodied in accordance with embodiment 10, a capillary tube made of an electric isolator is arranged between the flashtube and the tubular sheath body and a trigger wire is arranged within the capillary tube. A capillary tube may be used in conjunction with a tubular body made of an electrically conductive material such as stainless steel or aluminum in order to avoid a spark between the trigger wire and the tubular body. In particular, the tubular body may comprise or consist of at least one of a metal material, preferably stainless steel or aluminum, a ceramics material, or a polymer material, preferably polyether ether ketone (PEEK).

In an embodiment 12 according to the invention, wherein the flashlamp cartridge is embodied in accordance with embodiment 10 or 11, the tubular body comprises at least one axial end and the sheath further comprises at least one removable cartridge cap for closing the at least one axial end. The cap may be made of an electric isolator. The cap may comprise or consist of a sterilizable material. The cap may comprise or consist of a UV-resistant material. The tubular body may comprise or consist of an opaque material. In particular, the cap may comprise or consist of at least one of a ceramic material or a polymer material, preferably PEEK.

The sheath may include a tubular body and exactly one, exactly two or more caps. The tubular body may have a cylindrical cross-sectional shape. In particular, the tubular body may have a circular cylindrical cross-sectional shape. The at least one cap may have a cylindrical cross-sectional shape. In particular, the at least one cap may have a circular cylindrical cross-sectional shape. The tubular body and the caps may be concentrically and/or coaxially aligned.

At least one cap may form a port. At least one media connector may be formed on and/or in the at least one cap. The cap may comprise at least one protrusion and/or at least one recess for at least one media connector. The cap may comprise at least one protrusion and/or at least one recess to form at least one mounting feature. The at least one protrusion and/or at least one recess of the cap may be offset relative to the cap in an axial direction (of the cap and/or the cartridge) or in a radial direction (across, preferably orthogonal, relative to an axial direction). The cap may comprise at least one protrusion and/or at least one recess offset relative to the cap in the axial direction and at least one protrusion and/or at least one recess offset relative to the cap in the radial direction. At least one media connector may be arranged at the cap and face the axial direction to provide a connection to an interface of a decontamination unit in the axial direction. At least one media connector may be arranged at the cap and face the radial direction to provide a connection to an interface of a decontamination unit in the radial direction.

In an embodiment 13 according to the invention, wherein the flashlamp cartridge is embodied in accordance with one of the preceding embodiments, the sheath comprises a transparent window. The sheath may comprise exactly one transparent window. The transparent window may comprise or consist of glass, in particular quartz glass. The transparent window may be arranged in a center of the sheath in the axial direction. The transparent window may be arranged in a preferably radial aperture of the tubular body. The transparent window may sealingly close an aperture of the tubular body. The transparent window may be press fit and/or glued to the tubular body. The transparent window may have an outside surface aligned with an outside surface of the tubular body, in particular so as to form a common surface free of undercuts and/or acute angles. In an embodiment, the transparent window is attached to the sheath with an adhesive agent. The adhesive agent may comprise or consist of a polymer, in particular a heavily crosslinked polymer. The adhesive agent may be a cured epoxy resin.

The transparent window may be formed as cylinder sleeve-shaped axial section of the sheath. The transparent window may completely circumferentially surround the flashtube. The axial extension of the window may correspond to a distance between the electrodes, in particular the cathode and the anode, of the flashtube.

In an embodiment 14 according to the invention, wherein the flashlamp cartridge is embodied in accordance with embodiment 13, the components of the sheath other than the window are opaque.

In an embodiment 15 according to the invention, wherein the flashlamp cartridge is embodied in accordance with one of the preceding embodiments, the sheath comprises at least one mounting feature, in particular at least one radial protrusion and/or at least one axial protrusion, for correct alignment and orientation of the cartridge in a reception, such as a slot. The sheath may comprise at least one protrusion and/or at least one recess to form the at least one mounting feature. A protruding mounting feature may be a nose formed integrally with the sheath or a pin, dowel or the like attached to the sheath. The at least one mounting feature may be designed to relieve at least one media connector, preferably all media connectors, from mechanical stresses of holding the flashlamp cartridge to a decontamination unit.

In an embodiment according to the invention, wherein the flashlamp cartridge is embodied in accordance with one of the preceding embodiments, the sheath comprises at least one annular axially protruding mounting feature. An annular protrusion of the cartridge may be shaped complementarily with respect to an annular recess in a reception of a first or second socket of a decontamination unit. An annular protrusion of the cartridge may be shaped complementarily with respect to an annular recess in a reception of an interface of a decontamination unit. A cartridge may comprise a combination of an annular protruding mounting feature and one or more axially or radially protruding mounting features. The cartridge may have a first port with a first annular protrusion to be received by a reception of a first socket and a second port with a second annular protrusion to be received by a reception of a second socket of a second connector. The first and second annular protrusions of the cartridge may extend in different directions, in particular in diametrically opposite directions. An annular protrusion may extend completely circumferentially along the outer circumference of a particularly cylindrical cartridge. An annular protrusion may be arranged at a port of a cartridge such that one or more, in particular all, media connectors of this port are arranged radially within the annular protrusion. The annular protrusion of a port may extend further in the axial direction than one or more, particularly all, media connectors of the port. The utilization of an axial protrusion, particularly an annular protrusion, has been shown to be advantageous in protecting the media connectors of a port from mechanical damage. The annular protrusion may comprise or consist of a polymer material, in particular PEEK.

In an embodiment according to the invention, the flashlamp cartridge may comprise a mounting tab. The mounting tab may be connected in a hinged manner to the cartridge. The mounting tab may extend from the cartridge in a first position radial relative to the tubular body of the cartridge and/or in a second position axial relative to the tubular body of the cartridge. Preferably, the flashlamp cartridge comprises only one tab attached to a first or second axial end of the cartridge. Preferably, the flashlamp cartridge comprises only one tab attached to the first or second port of the cartridge.

In an embodiment 16 according to the invention, wherein the flashlamp cartridge is embodied in accordance with one of the preceding embodiments, a coolant chamber is arranged between the sheath, in particular the tubular body, and the flashtube. The coolant chamber may be concentrically and/or coaxially arranged between the flashtube and the sheath, in particular the tubular body. The coolant chamber may separate the flashtube from the sheath, in particular the tubular body, in the radial direction.

In an embodiment 17 according to the invention, wherein the flashlamp cartridge is embodied in accordance with embodiment 16, the coolant chamber extends from a coolant inlet to a coolant outlet. The coolant chamber may extend in the axial direction from a first cap to a second cap of the sheath. The coolant chamber may extend in the axial direction along the entire flashtube.

In an embodiment 18 according to the invention, wherein the flashlamp cartridge is embodied in accordance with embodiment 16 or 17, the coolant chamber annularly surrounds the flashtube, in particular so as to separate the flashtube from the sheath.

In an embodiment 19 according to the invention, wherein the flashlamp cartridge is embodied in accordance with one of embodiments 16 to 18, the coolant chamber is filled with a gaseous coolant. Preferably, the coolant chamber is free of any liquid coolant, in particular during active operation of the flashlamp cartridge for decontamination (i.e., while the electrodes of the flashlamp cartridge are supplied with a voltage).

In an embodiment 20 which relates to a decontamination unit according to one aspect of the invention, the decontamination unit comprises a housing enclosing a disinfection chamber, particularly for dry disinfection, an opening in the housing for insertion of a disinfection target into the disinfection chamber, a flashlamp, in particular a flashtube, preferably a flashlamp cartridge comprising a flashtube in accordance with at least one of the embodiments 1 to 19, for pulsed emissions of ultraviolet light. The flashlamp is arranged in the housing to irradiate the target within the disinfection chamber. According to an aspect of the invention, at least one slot is formed in an outside surface of the housing, the at least one slot extending into the disinfection chamber and receiving the flashlamp. The slot forms a recess that may be shaped corresponding to the flashlamp to be inserted into the recess. In particular, at least a section of the slot may be shaped corresponding to at least a section of the flashlamp cartridge in particular according to one of the embodiments 1 to 19, in particular to a section of a cap of the cartridge, such that a flashlamp, preferably a flashtube, of the cartridge is arranged to irradiate the target within the disinfection chamber when the flashlamp is received in the at least one slot. The slot acts as a receiver for the flashlamp. The at least one slot may include at least one mounting feature correspondingly shaped to at least one mounting feature of the flashlamp, in particular the flashlamp cartridge, in particular of a cap of the cartridge, so as to determine the alignment and/or orientation of the flashlamp relative to the decontamination unit.

In one embodiment, the decontamination unit may be configured to be operated in a non-sterile environment. The disinfection chamber may realize a clean environment in accordance with clean room class ISO 6 or better, ISO 5 or better, ISO 4 or better, in accordance with DIN EN ISO 14644-1 (2015). The disinfection chamber may realize a clean environment in accordance with EU-GMP class D, C or better. The environment surrounding the decontamination unit may correspond to a less clean environment than that of the disinfection chamber.

In an embodiment 21 according to the invention, wherein the decontamination unit is embodied in accordance with embodiment 20, at least one socket is provided with an interface connected to the flashlamp and attached to the housing.

In an embodiment 22 according to the invention, wherein the decontamination unit is embodied in accordance with embodiment 21, the socket is attached to an outside surface of the housing, in particular to the outside surface in which the slot is formed.

In an embodiment 23 according to the invention, wherein the decontamination unit is embodied in accordance with embodiment 21 or 22, the socket covers the slot. In particular, the slot is entirely covered by the socket. The socket may form a barrier to UV radiation from within the disinfection chamber to the surroundings of the decontamination unit. The socket may form an air-tight barrier between the disinfection chamber and the surroundings of the decontamination unit, in particular with respect to an overpressure.

In an embodiment 24 according to the invention, wherein the decontamination unit is embodied in accordance with one of the embodiments 21 to 23, the socket releasably attaches the flashlamp firmly to the housing. In particular, at least a section of the socket may be shaped corresponding to at least a section of the flashlamp cartridge, in particular according to one of the embodiments 1 to 19, in particular to a section of a cap of the cartridge, to firmly hold the flashlamp.

In an embodiment 25 according to the invention, wherein the decontamination unit is embodied in accordance with embodiment 24, the interface comprises a mounting feature for defining a predefined orientation and/or alignment of the flashlamp relative to the housing. The interface may include at least one mounting feature correspondingly shaped to at least one mounting feature of the flashlamp, in particular the flashlamp cartridge, in particular of a cap of the cartridge, so as to determine the alignment and/or orientation of the flashlamp relative to the decontamination unit.

In an embodiment 26 according to the invention, wherein the decontamination unit is embodied in accordance with one of the embodiments 21 to 25, the interface contains at least one media connector for supplying the flashlamp, the media connector comprising at least one of (i) an electrode connector, (ii) a trigger connector, (iii) a ground connector, and (iv) a coolant connector.

In an embodiment 27 according to the invention, wherein the decontamination unit is embodied in accordance with one of the embodiments 21 to 26, the decontamination unit comprises a first socket and a second socket, wherein preferably the decontamination unit comprises exactly two sockets.

In an embodiment 28 according to the invention, wherein the decontamination unit is embodied in accordance with embodiment 27, the first socket defines a first interface and the second socket defines a second interface different from the first interface.

In one embodiment, one of the first or second sockets may receive a mounting tab of the flashlamp cartridge. In one embodiment, one of the first or second interfaces may receive a mounting tab of the flashlamp cartridge. The mounting tab may be firmly, particularly rigidly or in a hinged manner, attached to the flashlamp cartridge. The mounting tab may be a bracket, lug, ear, strap or the like, which extends in a direction radial relative to the axial extension of the flashlamp cartridge. The tab may improve handling of the cartridge by providing a handle for a manual operator to firmly grip the optionally axially cylindrical cartridge for inserting the cartridge into a decontamination unit and/or for removing the cartridge from the decontamination unit.

In an embodiment 29 according to the invention, wherein the decontamination unit is embodied in accordance with embodiment 28, only one of the first socket and the second socket comprises a coolant supply line wherein the other one comprises a coolant discharge line.

In an embodiment 30 according to the invention, wherein the decontamination unit is embodied in accordance with embodiment 29, the coolant supply line and the coolant discharge line are filled with a gaseous coolant. Preferably, the supply line and the coolant discharge line are free of any liquid coolant, in particular during active operation of the flashlamp cartridge for decontamination (i.e., while the electrodes of the flashlamp are supplied with a voltage).

In an embodiment 31 according to the invention, wherein the decontamination unit is embodied in accordance with one of the embodiments 28 to 30, the first socket and the second socket comprise different mounting features for defining a predefined orientation and/or alignment of the flashlamp relative to the first and second socket.

In an embodiment 32 according to the invention, wherein the decontamination unit is embodied in accordance with one of the embodiments 28 to 31, only one of the first socket and the second socket comprise a trigger connector.

In an embodiment 33 according to the invention, wherein the decontamination unit is embodied in accordance with one of the embodiments 20 to 32, the slot firmly holds the flashlamp.

In an embodiment 34 according to the invention, wherein the decontamination unit is embodied in accordance with one of the embodiments 20 to 33, the decontamination unit comprises a first slot and a second slot, wherein preferably the decontamination unit comprises exactly two slots.

In an embodiment 35 according to the invention, wherein the decontamination unit is embodied in accordance with embodiment 34, the first slot and the second slot pierce different inside surfaces of the disinfection chamber.

In an embodiment 36 according to the invention, wherein the decontamination unit is embodied in accordance with embodiment 35, the first slot and the second slot pierce inside surfaces of the disinfection chamber opposite relative to one another.

In an embodiment 37 according to the invention, wherein the decontamination unit is embodied in accordance with embodiment 35 or 36, the first slot and the second slot align. In particular, the first and second slots align coaxially.

In an embodiment 38 according to the invention, wherein the decontamination unit is embodied in accordance with one of the embodiments 33 to 37, the first slot and the second slot receive the same flashlamp, in particular the same flashtube, in particular the same flashlamp cartridge in accordance with one of the embodiments 1 to 19.

In an embodiment 39 according to the invention, wherein the decontamination unit is embodied in accordance with one of the embodiments 20 to 38, a sheath separates the flashlamp from a section of the disinfection chamber receiving the disinfection target. In particular, the sheath is the sheath of a flashlamp cartridge in accordance with one of the embodiments 1 to 19.

In an embodiment 40 according to the invention, wherein the decontamination unit is embodied in accordance with embodiment 39, the sheath includes an opaque section and a transparent window.

In an embodiment 41 according to the invention, wherein the decontamination unit is embodied in accordance with one of the embodiments 20 to 40, a sealing member such as an o-ring is arranged between the flashlamp, in particular a sheath of the flashlamp, preferably the sheath of the cartridge in accordance with one of the embodiments 1 to 19, and the housing to close the disinfection chamber. In particular, the decontamination unit is provided with at least one sealing member to seal each slot such that a gas-tight separation is formed between the disinfection chamber and the environment surrounding the decontamination unit. In an embodiment of a decontamination unit comprising a flashlamp cartridge including a tubular sheath body and at least one sheath cap, the sealing member may be arranged such that the cap is arranged on the far side of the sealing member relative to the disinfection chamber.

In an embodiment 42 according to the invention, wherein the decontamination unit is embodied in accordance with one of the embodiments 20 to 41, the opening defines a flat target area and the flashlamp, in particular a flashtube and/or a transparent window, particularly a window of a cartridge, is offset relative to the target area. A flat target area may correspond to a section or component of a medical or foodstuff container target, such as a cap, lid, plate, bottom, wall or the like. A flat target area may correspond to a surface of a foodstuff product target. The opening may be called a tunnel. The flat target area may correspond to the cross-sectional area of the tunnel. The flat target area defines a plane and a normal direction relative to the plane. The plane may be constrained by the extension of the target or the extension of the tunnel. The flashlamp may be offset radially relative to a central axis of the target area for a distance farther than the extension of the target area. The flashlamp may be offset an angle relative to the normal direction. For example, the flashlamp may be arranged behind a transparent window relative to the target area, wherein the window may define a median radiation direction of the flashlamp. The median radiation direction can be at an angle of at least 10°, or at least 30°, relative to the normal direction. The median radiation direction can be at an angle of at most 80°, or at most 60°, relative to the normal direction.

In an embodiment 43 according to the invention, wherein the decontamination unit is embodied in accordance with embodiment 42, the flashlamp is offset radially relative to the target area.

In an embodiment 44 according to the invention, wherein the decontamination unit is embodied in accordance with embodiment 42 or 43, the target area defines a normal, in particular perpendicular, central axis wherein the flashlamp is offset angularly relative to the target area at least 10°, at least 30° and/or at most 60°, or at most 80°.

In an embodiment 45 according to the invention, wherein the decontamination unit is embodied in accordance with one of the embodiments 20 to 44, the disinfection chamber is kept at an overpressure. The overpressure may be at least 1 bar, at least 2 bars or at least 3 bars. In particular, the overpressure may be approximately 4 bars.

In an embodiment 46 according to the invention, wherein the decontamination unit is embodied in accordance with one of the embodiments 20 to 45, the flashlamp is a flashtube contained within a cartridge according to one of the embodiments 1 to 19.

In an embodiment 47 according to the invention, wherein the decontamination unit is embodied in accordance with embodiment 46, a positive connection is provided for holding the cartridge. In particular, the socket(s) and the cartridge correspond to one another to form a positive connection.

In an embodiment 48 according to the invention, wherein the decontamination unit is embodied in accordance with embodiment 47, the slot and the cartridge correspond to one another to form a positive connection.

In an embodiment 49 according to the invention, wherein the decontamination unit is embodied in accordance with one of the embodiments 20 to 48, exactly one flashlamp is provided.

In an embodiment 50 according to the invention, wherein the decontamination unit is embodied in accordance with one of the embodiments 20 to 49, the disinfection chamber has at least one reflective inner surface. In particular, more than one inner surface of the disinfection chamber is reflective. In particular, all of the inner surfaces of the disinfection chamber are reflective.

In an embodiment 51 according to the invention, wherein the decontamination unit is embodied in accordance with embodiment 50, the reflective inner surface is coated with a reflective coating. A reflective coating may be a gold coating, an aluminum coating, or the like. Preferably, the reflective coating reflects at least 99% of the ultraviolet radiation emitted by the flashlamp. Preferably, the reflective coating reflects at least 90% or at least 99% of all of the radiation emitted by the flashlamp.

In an embodiment 52 according to the invention, wherein the decontamination unit is embodied in accordance with embodiment 50 or 51, the reflective inner surface is a polished metal, in particular aluminum or stainless steel.

In an embodiment 53 according to the invention, wherein the decontamination unit is embodied in accordance with one of the embodiments 20 to 52, a power supply for operating the flashlamp is arranged remote from the decontamination unit.

In an embodiment 54 according to the invention, wherein the decontamination unit is embodied in accordance with one of the embodiments 20 to 53, a sensor is provided for detecting the ultraviolet light irradiation within the disinfection chamber.

In an embodiment 55 according to the invention, wherein the decontamination unit is embodied in accordance with embodiment 54, the sensor measures the ultraviolet light irradiation.

In an embodiment 56 according to the invention, wherein the decontamination unit is embodied in accordance with embodiment 54 or 55, the sensor determines if the ultraviolet light irradiation exceeds a predetermined dosage threshold. The sensor may cause a warning signal if the ultraviolet light irradiation exceeds a (upper, first) predetermined dosage threshold. The sensor may cause a warning signal if the ultraviolet light irradiation does not exceed a (lower, second) predetermined dosage threshold.

In an embodiment 57 according to the invention, wherein the decontamination unit is embodied in accordance with one of the embodiments 20 to 56, the decontamination unit is free of any disinfection fluid discharge.

In an embodiment 58 according to the invention, wherein the decontamination unit is embodied in accordance with one of the embodiments 20 to 57, the decontamination unit further comprises one or more processing components for manipulating the disinfection target. Manipulating may include thermal manipulation and/or mechanical manipulation.

An embodiment 59 according to an aspect of the invention relates to a decontamination array comprising multiple decontamination units of one of the embodiments 20 to 58 and a controller operating the multiple decontamination units. The controller may be an analogue controller, a digital controller, or a mixture thereof. The controller may comprise a microprocessor or a microcontroller. The controller may comprise a digital level controller (DLC).

In an embodiment 60 according to the invention, the decontamination array of embodiment 59 further comprises a support structure carrying the decontamination units and an actuator causing the support structure to perform a repetitive motion. The repetitive motion may be a linear back and forth movement. The repetitive motion may include a first back and forth movement along a first movement axis, which may be a horizontal movement axis or a vertical movement axis. The repetitive motion may include a second back and forth movement along a second movement axis, which may be a horizontal movement axis or a vertical movement axis.

In an embodiment 61 according to the invention, the support structure of the decontamination array of embodiment 60 is a revolving wheel.

In an embodiment 62 according to the invention, the decontamination array of one of the embodiments 59 to 61 further comprises one single power supply for operating the multiple decontamination units.

In an embodiment 63 according to the invention, the controller of the decontamination array of one of the embodiments 59 to 62 triggers the individual flashlamps of the decontamination units at a frequency of less than 1 Hz, less than ½ Hz, preferably approximately ⅓ Hz.

In an embodiment 64 according to the invention, the controller of the decontamination array of one of the embodiments 59 to 63 triggers the individual flashlamps in a cascading manner and/or one after another. Triggering in a cascading manner may indicate that the flashlamps are triggered at different points in time, for example one after another, for instance in a clockwise or counterclockwise manner with respect to the repetitive motion of the support structure. Triggering one after another may indicate that only one of the multiple decontamination units' flashlamps is ever triggered at any given time, in particular such that only one of the multiple decontamination units emits a flash at any given time.

In an embodiment 65 according to the invention, the controller of the decontamination array of one of the embodiments 59 to 64 triggers the individual flashlamps based on a predetermined trigger position of an individual decontamination unit along the repetitive motion. For example, each individual decontamination unit may be triggered upon reaching a certain trigger position stationary with respect to the repetitive movement of the support structure. In particular, the controller may trigger an individual flashlamp after the respective decontamination unit has reached or passed a trigger position along its repetitive path of movement. If the units are held by a revolving wheel-like support structure, a single trigger position may be defined stationary with respect to the wheel-like support structure to cause the controller to trigger each individual decontamination unit when or after it reaches the trigger position. Each decontamination unit may be operated at a repetitive processing cycle including at least one ultraviolet flash light decontamination step. Each ultraviolet flash light decontamination step may comprise the emission of at least one pulsed emission. Each ultraviolet flash light decontamination step comprises the emission of at most four or five pulsed emissions. In particular, each ultraviolet flash light decontamination step may comprise the emission of exactly two or exactly three pulsed emissions.

In an embodiment 66 according to the invention, the decontamination array of one of the embodiments 59 to 65 comprises at least 10, at least 20, and/or at most 100, at most 50, preferably 20 to 40 decontamination units.

In one embodiment 67 according to the invention, wherein the decontamination array is embodied in accordance with one of the embodiments 59 to 66, each decontamination unit may be operated at a repetitive processing cycle including at least one ultraviolet flash light decontamination step and at least one further processing step utilizing processing equipment for manipulating a target within the disinfection chamber of the respective decontamination unit. A cycle may take at least 1 second and at most 5 seconds, preferably at least 2.0 seconds and at most 3.5 seconds. The at least one ultraviolet flash light decontamination step may take between 0.01 seconds and 0.5 seconds, particularly 0.05 seconds to 0.3 seconds, preferably 0.15 to 0.25 seconds. The further processing steps may include at least one of a target insertion step for introducing the target through the tunnel into the disinfection chamber, a target exit step for removing the target through the tunnel from the disinfection chamber, a mechanical processing step, and a thermal processing step.

Flashlamp

A flashlamp as described herein with relation to the invention generally refers to a light source capable of emitting short light pulses or flashes. A flashlamp produces intense, incoherent light emissions for a short duration of time. The duration of the flash or pulsed light emission may last for at least 0.1 µs, at least 0.3 µs, at least 0.5 µs, or at least 0.6 µs. The duration of the flash or pulsed light emission may last for less than 10 µs, less than 5 µs, less than 2 µs, or less than 1.5 µs, optionally even less than 1 µs or less than 0.8 µs.

A flashlamp comprises two electrodes, namely a cathode and an anode. Furthermore, a flashlamp comprises a trigger. The anode and the cathode are contained within a sealed glass envelope (bulb) filled with a gas. The glass envelope may be made of fused quartz, borosilicate glass or quartz glass. Quartz glass may also be called synthetic silica glass. The gas may be a noble gas, including Argon, Xenon, or Krypton. The flashlamp is filled with a gas that, when triggered, ionizes and conducts a high voltage pulse to produce the light. The gas within the flashlamp may exhibit extremely high electrical resistance such that the flashlamp will not conduct electricity from the anode to the cathode until the gas is ionized. Once triggered, the gas is ionized and a spark or arc forms between the electrodes, allowing the voltage supply, particularly the capacitor, to discharge. The trigger induces ionization of the gas within the flashlamp. The trigger may be an antenna-like probe to stabilize and/or facilitate the arc of the flashlamp.

Flashtube

A flashtube in accordance with the invention described herein is a specific type of flashlamp with the generally cylindrical and longitudinal design. A flashtube may be generally straight. The flashtube may define an axial extension. A flashtube may be made of a length of glass tubing with electrodes (capacitors) at either end. The glass envelope of a flashtube may preferably have the shape of a circular hollow cylinder. The electrodes, i.e., the anode and the cathode, of the flashtube are arranged at opposite ends of the flashtube. The electrodes may be arranged at the axial opposite ends of the flashtube. The electrodes protrude into each end of the tube. The electrodes are sealed to the glass envelope (bulb) of the flashtube. Along the axial length of the flashtube, and intermittent space separates the anode from the cathode in the axial direction. The arc is formed in the intermittent space. The electrodes of the flashlamp may be connected to a voltage supply, such as a capacitor, which may be charged with relatively high voltage (between 250 and 5,000 V or more). Preferably, the electrodes may be charged with a high voltage between 700 V and 1,100 V, more preferably between 750 V and 950 V, particularly between 800 V and 900 V.

Ultraviolet (UV) Light

A flashlamp, particularly a flashtube, according to the invention emits ultraviolet light.

According to DIN 5031-7, ultraviolet (UV) radiation refers to wavelengths from 10 nm to 380 nm. UV-A radiation may refer to ultraviolet light in the range of 315 to 380 nm. UV-B-radiation may refer to the range of 280 to 315 nm. UV-C radiation may refer to the range of 100 to 280 nm. EUV radiation may refer to the range of 10 nm to 121 nm. According to the present invention, the range of 200 nm to 300 nm may be preferred.

The flashlamp, particularly the flashtube, according to the invention emits radiation at least some of which, preferably most of which (most of which meaning 50% or more) has a wavelength between 10 nm and 1,110 nm. At least some of the radiation emitted by a flashlamp in accordance with the invention has a wavelength in the ultraviolet range of 10 nm to 380 nm. Preferably, most (at least 50%) of the light emitted by the flashlamp according to the invention has a wavelength in the range of 10 nm to 380 nm.

Cartridge

A cartridge in accordance with the invention refers to a container surrounding the flashlamp. Within the cartridge, the flashlamp including its glass envelope is completely contained. The cartridge comprises a sheath encapsulating the flashlamp, which may preferably be a flashtube. The cartridge may consist of a sheath encapsulating the flashlamp, which may preferably be a flashtube. For example, the cartridge may comprise a capped tube as a sheath surrounding the glass envelope of the flashlamp. The cartridge may be designed such that the flashlamp is inoperable when the sheath is removed. The cartridge may be designed such that the flashlamp and the sheath are reversibly attached to one another. The cartridge can be designed such that the sheath and the flashlamp are irreversibly attached to one another (i.e., the removal of the sheath from the flashlamp can only be performed by destructive means). Preferably, the cartridge is designed to withstand an overpressure atmosphere surrounding the cartridge of at least 2 bars, at least 3 bars, or at least 4 bars.

Sheath

The sheath may comprise one or more materials different from the glass envelope of the flashlamp. The flashlamp cartridge forms a unit consisting of the flashlamp, particularly the flashtube, and the sheath encapsulating the flashlamp. The sheath may preferably be a solid barrier. It shall be clear that the sheath is separate from and/or different from the glass envelope of the flashlamp, particularly the flashtube. The sheath may be made of one or more mechanically rigid materials. The sheath material may be a sterilizable material. Suitable sheath materials include materials such as stainless steel, aluminum, PEEK, ceramic, and glass. It is conceivable that the sheath comprises or consists of glass material, for example fused silica glass, borosilicate glass or quartz glass.

The sheath may shield the flashlamp from environmental effects, including at least one of electricity, mechanical forces, chemical contamination, biological contamination, and chemical degradation. The sheath may prevent uncontrolled direct environmental contact to the flashlamp, particularly the flashtube, contained therein, particularly including contact with at least one of dust, air, water, electrical current, and mechanical forces.

The sheath may be made of opaque material and be equipped with a transparent window. The terms "opaque" and "transparent" in the context of the present invention are related to the ability or inability to transmit light in the ultraviolet range.

Sterilizable Material

Sterilizable materials include materials that can be subjected to decontamination measures including ultraviolet light decontamination and chemical decontamination using decontamination fluid, repeatedly and preferably without any unacceptable degradation. Sterilizable materials are particularly materials from which microorganisms can efficiently be removed. Sterilizable materials include materials such as stainless steel, aluminum, PEEK, ceramic, and glass. A sterilizable material may be an electro-polished metal material, in particular electro-polished stainless steel or aluminum.

Port

In accordance with the invention, the cartridge may be equipped with a port providing a controlled gateway through the barrier of the cartridge in the form of the sheath to allow for supply to the flashlamp. The port or ports may be the exclusive way to transmit media into and/or out of the sheath. Media may include electricity such as the voltage for supplying the electricity to the trigger for ionizing the gas or the electricity for operating a sparker, insofar as one is used. Media may include a coolant, including fluid coolants and/or gaseous coolants. A fluid coolant may be water, particularly deionized water. A gaseous coolant may be nitrogen or ambient air. In a preferred embodiment, at least one of the flashlamp cartridge and the decontamination unit is entirely free of any fluid coolant.

Media Connector

A media connector may include a protrusion or an orifice. A media connector may be a pin, a plug, and an orifice optionally surrounded by a seal or the like. The media connector may be connected to an electrode, trigger, or the like. A media connector of the flashlamp, in particular the flashlamp cartridge, may be formed integrally with a component of the flashlamp, particularly of the flashtube. For example, an electrode of the flashlamp may comprise a section extending out of the flashlamp and through the sheath to act as a media connector. A media connector may be an electric connection such as a ground connector, for example a reference ground connection or a safety ground connection. A ground connector may be provided to connect electrically conductive parts of the cartridge, for example a stainless-steel tubular body of the sheath, to a ground line for reference and/or safety grounding of the electrically conductive parts.

Housing

The decontamination unit comprises a flashlamp and a housing enclosing a disinfection chamber. The housing may shield the environment surrounding the decontamination unit from the ultraviolet light emission of the flashlamp. The housing encloses the disinfection chamber as well as the flashlamp. If the flashlamp is part of a flashlamp cartridge, the housing may enclose the flashlamp cartridge. The housing may be of generally cubic shape. The housing may be of a different shape. The housing contains at least one chamber, wherein the chamber is surrounded by one or more wall sections of the housing. For example, in case the housing is of a generally cubic shape, the chamber within the housing may be confined by six wall sections of the housing. It shall be made clear that the general geometrical configuration of the housing and of the chamber is selected for the purpose of efficient manufacturing, assembly, and decontamination within the chamber so that the geometrical property offers a wide range of different options.

The housing has at least one opening through one wall section thereof for insertion of a disinfection target into the disinfection chamber and/or for removal of a disinfection target out of the disinfection chamber. The opening may be called a tunnel. The cross-sectional area of the tunnel may be as large as or smaller than the cross-section of the disinfection chamber. The housing may have exactly one tunnel. The housing, particularly its opening, may be free of any guiding tubes or other guides for the target.

The housing may shield the disinfection target within the disinfection chamber from environmental influences. Environmental influences may include mechanical influences, biological contamination, chemical contamination, or the like, while the disinfection target is arranged within the disinfection chamber. The disinfection unit may be provided with a supply of pressurized clean air so that the disinfection chamber is constantly held at an overpressure. The overpressure is larger than the ambient air pressure in the environment of the processing unit. The overpressure may exceed 2 bars. The overpressure may exceed 3 bars. The overpressure may exceed 4 bars. Preferably, the overpressure is less than 10 or less than the 5 bars. The overpressure may provide a constant flow of air from a clean air source through the disinfection chamber and any apertures thereof, including the opening or tunnel, to the environment surrounding the decontamination unit. By flooding the disinfection chamber with clean air, any contamination of the disinfection target within the disinfection chamber by contaminated air can be prevented.

The housing may hold additional target processing equipment, including target manipulation equipment for manipulating the target within the disinfection chamber. Target manipulation equipment may include thermal manipulation equipment. Thermal manipulation equipment may thermally manipulate the disinfection target, for example heat or cool the disinfection target. Target manipulation equipment may include mechanical manipulation equipment. Mechanical manipulation equipment may be designed to mechanically act upon the disinfection target. Mechanical manipulation equipment may move the disinfection target, including linear movement and rotational movement. Mechanical manipulation equipment may mechanically process the disinfection target. Mechanical processing may include the addition of material to the disinfection target or the removal of material from the disinfection target. It shall be clear that mechanical manipulation equipment or thermal manipulation equipment as described herein acts upon the disinfection target within the disinfection chamber.

The housing may have one or more slots formed in an outside surface of the housing extending through the wall section of the housing into the disinfection chamber.

The term "outside surface" generally refers to a surface of the housing facing the environment surrounding the decontamination unit. The term "inside surface" generally refers to a surface of the housing facing the disinfection chamber of the decontamination unit. The disinfection chamber is confined by the one or more inside surfaces of the housing.

Slot

The slot or slots is or are designed for receiving the flashlamp, particularly the flashlamp cartridge. In one embodiment, which can be combined with the aforementioned, the housing comprises exactly one or exactly two slots extending into the disinfection chamber into which the aforementioned tunnel leads.

It may be preferred that the at least one slot and a flashlamp cartridge correspond to one another. The cartridge and the at least one slot may correspond to one another in that the cartridge may be exclusively inserted into the slot in a predetermined orientation and/or alignment. The cartridge and the at least one slot may correspond to one another such that, when the cartridge is received within the receiver, the slot is sealed in an airtight manner. The cartridge and the at least one slot may correspond to one another in that they are matched to form a positive connection. The cartridge and the slot may correspond to one another so that the cartridge received in the at least one slot is restricted from movement in at least one direction, preferably a radial direction or a rotational direction. The cartridge and the slot may correspond to one another so that the cartridge received in the at least one slot is restricted to predetermined movement, particularly in only one direction, for example to predetermined movement in an axial direction.

Interface

An interface may include a mechanical connection of the socket for attaching the flashlamp, in particular the flashlamp cartridge. The flashlamp, in particular the flashlamp cartridge, and/or the interface may comprise at least one mounting feature, such as a protrusion or recess, generally called a mount. The flashlamp, in particular the flashlamp cartridge, and/or the interface may comprise cooperating mounting features. A mounting feature may comprise a dowel. A mounting feature may comprise a nose integrally formed with the interface or the sheath.

Alternatively, or additionally, the interface may comprise one or more media connectors of the socket for supplying the flashlamp, in particular the flashlamp cartridge. A socket may have one or more media connectors corresponding to the one or more media connectors of a flashlamp cartridge port.

An interface of a socket may be designed to correspond to a port of a flashlamp cartridge. The decontamination unit may be equipped with a first interface to exclusively correspond to a first port of a flashlamp cartridge. Additionally, the decontamination unit may be equipped with a second interface to exclusively correspond to a second port of the flashlamp cartridge. An interface and a port may correspond to one another in a pin-and-plug like manner. A flashlamp cartridge may be rendered operable by attaching the at least one port to the corresponding at least one interface.

BRIEF DESCRIPTION OF THE DRAWINGS

The following schematic drawings show aspects of the invention for improving the understanding of the invention in connection with some exemplary illustrations. Further embodiments, features and technical aspects are described below. Further details of preferred embodiments of the invention as shown in the enclosed figures in which:

FIG. 4A is a front view of a disinfection unit according to the invention;

FIG. 5A is a first cross-sectional view of the decontamination unit along line A-A of FIG. 4A;

DETAILED DESCRIPTION OF THE DISCLOSURE

Figure 1:
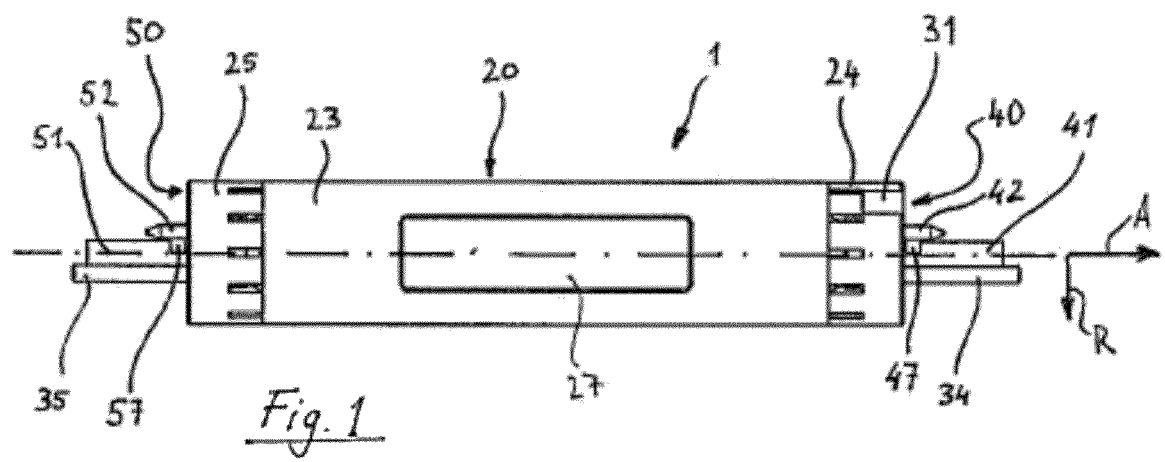
FIG. 1 is an illustration of the flashlamp cartridge in accordance with the invention.

In the following description of preferred embodiments according to the invention, similar or identical components are designated with the same or similar reference number.

The flashlamp cartridge in accordance with the invention is generally designated with reference 1. The decontamination unit in accordance with the invention is generally indicated with reference 100. The main components of the flashlamp cartridge 1 according to the invention are a flashtube 10 for pulsed emissions of ultraviolet light and a sheath 20 encapsulating the flashtube 10.

The sheath 20 may comprise a tubular body 23 of general cylindrical cross-sectional area defining an axial direction A and a direction radial R radial relative to the axial direction A. In the axial direction A the opposing ends of the tubular body 23 of the sheath 20 may be closed by a respective cap 24, 25. Thus, the flashtube 10 can be entirely surrounded in the radial direction R along its entire axial length by the tubular body 23 and surrounded in the axial direction at both opposite ends along its entire cross-sectional area by the caps 24 and 25, respectively. The sheath 20 prevents any uncontrolled contact between the flashtube 10 contained therein and environmental media including liquids, gases, and electricity.

In order to supply the flashtube 10 with the electricity required for its operation, the flashlamp cartridge 1 according to the invention may be supplied with one or more ports 40, 50 having one or more gateways for media. In accordance with the exemplary embodiment indicated in the drawings, the flashlamp cartridge 1 comprises exactly two ports 40 and 50 that are realized by the caps 24 and 25. Each cap 24, 25 is provided with a number of media connectors 41, 42, 43, 44, 51, 52, 54. The media connectors 41, 51 comprise electrode connectors to supply the electrodes, a cathode 4 and an anode 5, within the flashtube 10, with an operating voltage of several hundred Volts.

In the present example, the right cap 24 further comprises the trigger connector 43 through which a trigger wire 3 leads. The trigger wire 3 may have a radius of approximately 0.25 mm. In the present example, the tubular body 23 of the sheath 20 may consist of stainless steel. In such an embodiment, where the tubular body 23 is capable of conducting electricity, it may be preferable that the trigger wire 3 is contained within a capillary tube 13 consisting of an isolator, such as quartz glass. Such a capillary tube 13 may have an inner radius of 0.35 mm.

The sheath 20 including both the tubular body 23 as well as the caps 24 and 25, may have a diameter of at least 5 mm, in particular at least 10 mm, preferably at least 15 mm and/or at most 100 mm, in particular at most 50 mm, preferably at most 20 mm. In the present example, the diameter may be approximately 17 mm. The length of the sheath 20 in the axial direction a may be at least 50 mm, in particular at least 75 mm and/or at most 150 mm, in particular at most 100 mm. For example, the length may be approximately 86 mm. The diameter of the electrode connectors 41, 51 may be larger than 2 mm, in particular larger than 3 mm, and/or less than 12 mm, in particular less than 8 mm.

The flashtube 10 comprises an envelope 17 of the glass material, in particular quartz glass material. Quartz glass is particularly transmissive for ultraviolet radiation, in particular in the range of 200 nm to 300 nm. The glass envelope 17 is sealingly connected to enclose the anode 5 and cathode 4 of the flashtube 10. The interior 16 of the flashtube 10 is filled with a noble gas, preferably Xenon.

The flashtube 10, particularly the glass envelope 17 thereof, may be separated from the tubular body 23 of the sheath 20 by a coolant chamber 26 surrounding the flashtube 10. The coolant chamber 26 extends radially between the glass envelope 17 and the tubular body 23. In the axial direction A, the coolant chamber 26 extends from the right cap 24 to the left cap 25. Each cap 24, 25 comprises as one of its respective media connectors a coolant connector 44, 54, one of which serves as an inlet and the other one of which serves as an outlet for the coolant. It may be preferred that the coolant is a coolant gas, particularly nitrogen or ambient air.

The tubular body 23 may have an annular groove at either axial end to receive an engagement portion of the respective cap 24, 25. The caps 24, 25 may consist of PEEK. A cap 24, 25 may comprise one or more clip portions to engage a recess, such as an annular groove, of the tubular body 23 for attaching the cap 24, 25 to the tubular body 23.

The tubular body 23 as well as the right or first cap 24 and the left or second cap 25 are opaque for ultraviolet radiation. The flashlamp cartridge 1 comprises a window 27 transparent for ultraviolet radiation such that the light emitted by the flashtube 10 encapsulated within the flashlamp cartridge 1 may leave it. The window 27 may extend in the axial direction A from the cathode 4 to the anode 5 of the flashtube 10. The window 27 forms a portion of the sheath 20 separating the flashtube 10 within the sheath 20 from the surroundings of the flashlamp cartridge 1 including, for example, a disinfection chamber 110. Between an axial end of the sheath 20 and the window 27, a sealing member such as an o-ring 28 may be arranged such that, when the flashlamp cartridge 1 is fit into a receiver, for example a slot 114, 115 of the housing 120 of the decontamination unit 100, the sealing member separates the environment surrounding the decontamination unit 100 and the disinfection chamber 110 therein. In contrast to the embodiment shown in FIG. 3, the flashlamp cartridge 1 of FIG. 1 is not equipped with sealing members. As an alternative to providing sealing members on the flashlamp cartridge 1, sealing members could be dispensed with or be attached to the housing 120.

Figure 2:
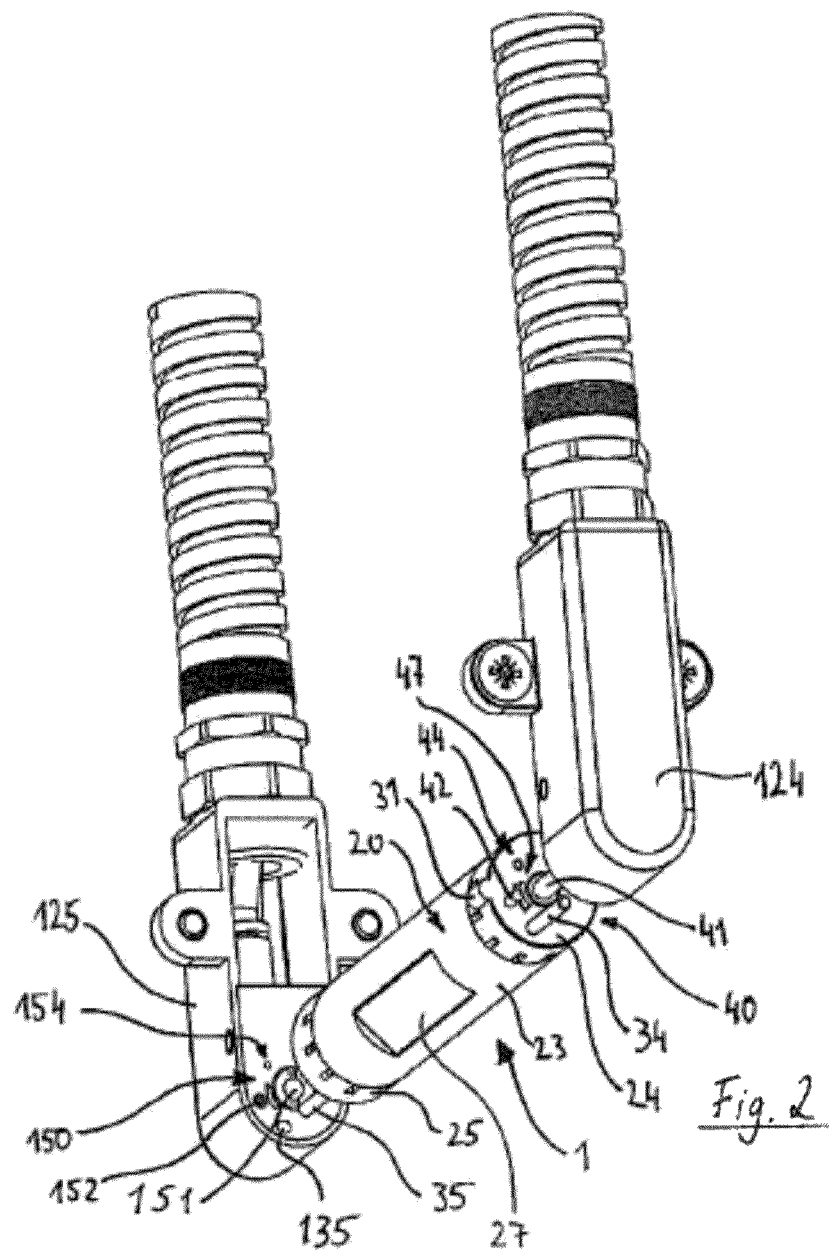
FIG. 2 is a perspective view of the flashlamp cartridge shown in FIG. 1 arranged between two sockets.
Figure 3:
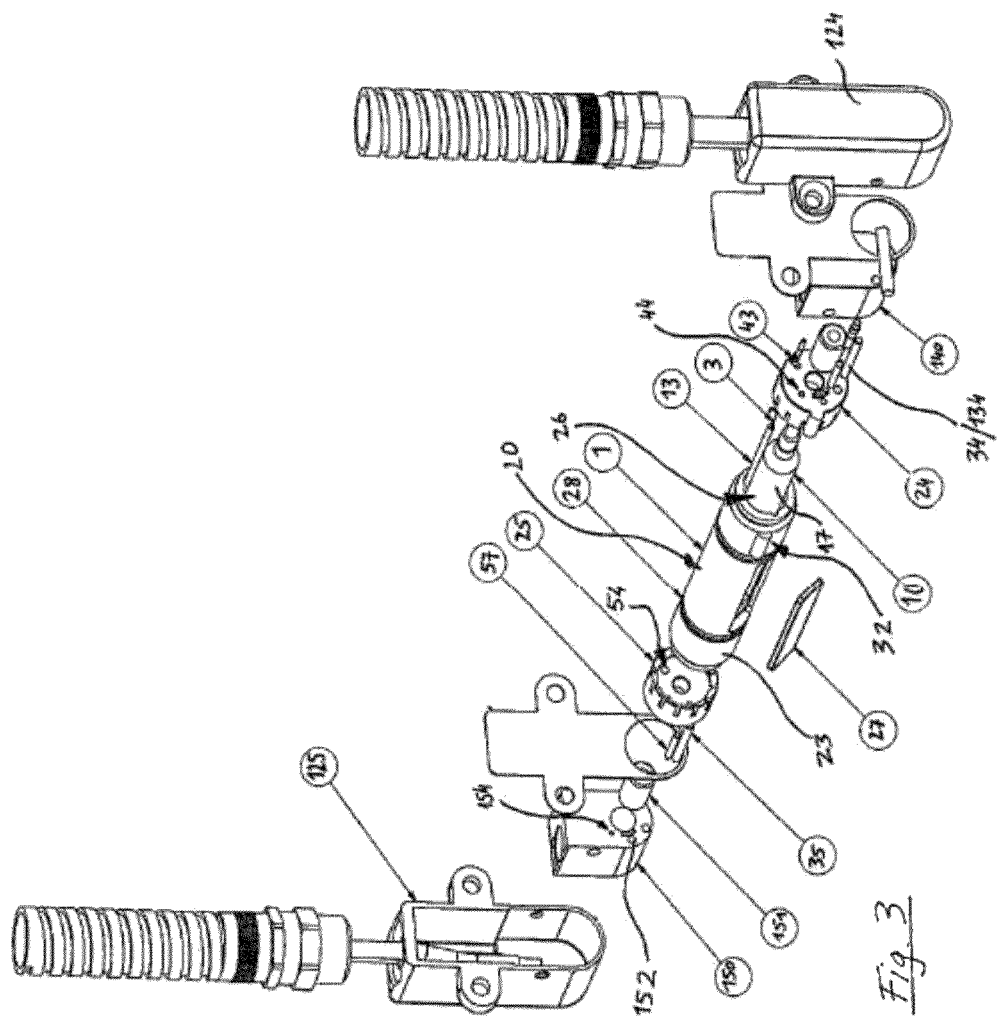
FIG. 3 shows an exploded view of another embodiment of a flashlamp cartridge according to the invention between two sockets.
Figure 5B:
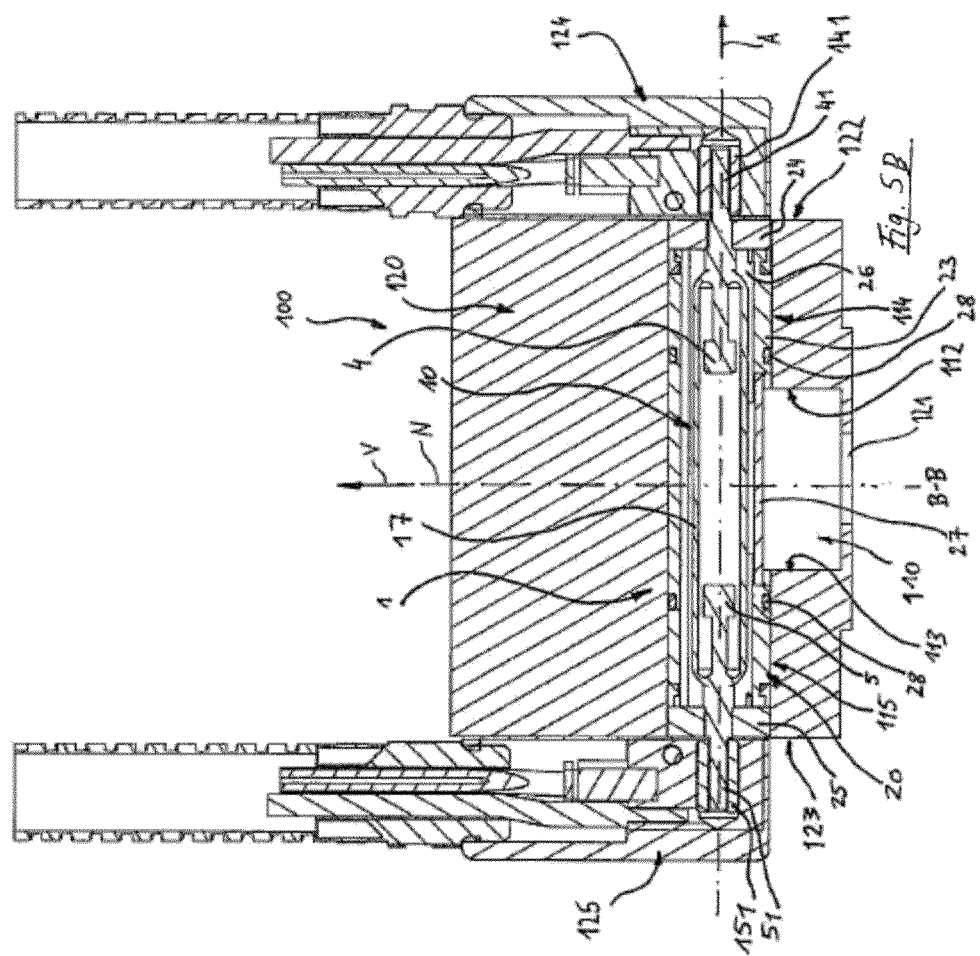
FIG. 5B is a second, schematic cross-sectional view through the housing of the decontamination unit of FIG. 4B along line C-C.

As can best be seen in FIG. 5B, the electrodes 4, 5, their connectors 41, 51, the flashtube 10, and the sheath 20 may all be coaxially aligned around a common axis in the axial direction A. The flashlamp cartridge 1 may be equipped with one or more mounting features. For example, the flashlamp cartridge 1 may be equipped with radially protruding mounting features 31, 32 as shown in FIGS. 2 and 3. The mounting feature 31 is formed integrally with the first cap 24 of the sheath 20. The second cap 25 in the present example is free of any radially extending mounting feature, such as the mounting feature 31 of the first cap 24. Thereby, the flashlamp cartridge 1 is prevented from being inserted into a receiver in the wrong way. Radially extending mounting features, such as the mounting feature 32, may also be provided on the exterior of the tubular body 23. The flashlamp cartridge 1 shown in FIG. 1 differs from the flashlamp cartridge 1 shown in FIG. 3 in that the flashlamp cartridge 1 of FIG. 1 is devoid of any mounting feature on the exterior of the tubular body 23.

The ports 40, 50 of the flashlamp cartridge 1 may be equipped with media connectors serving as ground connectors or pins 42, 52. Between the first ground connector or pin 42 and the first electrode connector 41, an isolator 47 protruding in the axial direction A may be arranged so as to avoid any spark between the electrode connector 41 and the first ground pin 42. A second isolator 57 may be part of the second port 50 to avoid sparks between the second electrode connector 51 and the second ground pin 52. The first ground pin 42 and/or the second ground pin 52 may be provided to establish a ground connection for the flashlamp cartridge 1, in particular for any conductive members thereof, including for instance the metal tubular body 23. The caps 24, 25 may preferably be made of an isolator.

As indicated for example in FIGS. 1 and 2, the first port 40 differs from the second port 50. The media connectors of the first port 40 are arranged in a manner mirror-symmetrical to those of the second port 50. Further, the first port 40 may differ from the second port 50 in that it comprises a trigger connector whereas the second port 50 does not. Additionally, or alternatively, the caps 24, 25 may be provided with one or more different mounting features. Presently, the first cap 24 comprises a radially extending nose forming a radial mounting feature 31. The second cap 25 does not comprise any radially extending mounting feature. The first and the second caps 24 and 25 may both comprise axially extending mounting features 34 or 35, respectively, which, in a manner similar to the media connectors of the ports 40, 50, are arranged mirror-symmetrically. The different arrangement of the media connectors and/or mounting features on the caps 24 and 25 ascertain that the flashlamp cartridge 1 can only be mounted correctly into a receiver.

Figure 4B:
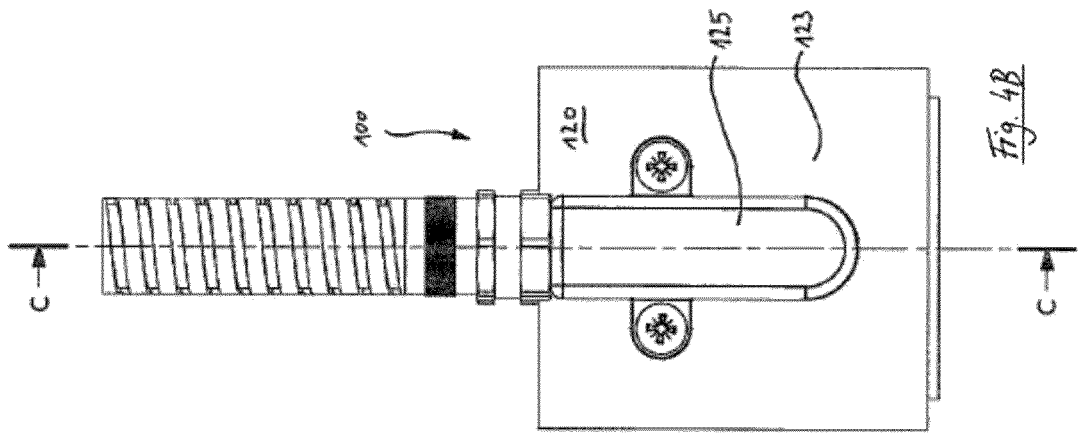
FIG. 4B is a side view of the decontamination unit of FIG. 4A.

FIGS. 4A and 4B show the decontamination unit 100 according to the invention from the outside and FIGS. 5A and 5B show cross-sectional views thereof. The decontamination unit 100 may be equipped with a flashlamp embodied in the flashlamp cartridge 1 comprising the flashtube 10. The decontamination unit 100 according to the invention may comprise a different flashtube.

In accordance with the invention, the decontamination unit 100 and the flashlamp shall be designed such that the flashlamp may be inserted for operation into the housing 120 of the decontamination unit 100 without disassembling the decontamination unit 100. To this end, the outside surface 122 or 123 of the housing 120 is provided with at least one slot 114, 115. The flashlamp shall be inserted from the outside via the slot 114, 115 into the housing 120. A socket 124, 125 or different cover may be provided to close a slot 114, 115 in which a flashlamp is received. The decontamination unit 100 may be provided with one or more interfaces 140, 150 for operatively connecting the flashlamp to one or more media connectors. An interface 140, 150 may be realized as part of a socket 124 or 125 removably attachable to the housing 120. Alternatively, at least one interface 140, 150 may be realized as a part of the housing 120, in particular being rigidly attached to the housing 120 or formed integrally with a component, such as a wall section, of the housing 120 (not shown in detail).

The flashtube 10 or other flashlamp may be directly mounted to the socket 124, 125. For example, the decontamination unit 100 according to the invention may include a flashlamp without a flashlamp cartridge 1. The decontamination unit 100 according to the invention may comprise a flashlamp, with or without the sheath 20. The decontamination unit 100 according to the invention may have all media connectors only on one end thereof. It may be preferred to use a flashlamp with media connectors on axially opposite ends as this configuration has been proven to be particularly suitable for tight spatial restraints.

The decontamination unit 100 comprises the housing 120. The housing 120 in the preferred example shown in FIGS. 4A through 4C and 5A through 5C has the opposite outside surfaces 122, 123 to each of which the respective socket 124, 125 is attached. As indicated in the drawings, the socket 124, 125 may be releasably attached to the housing 120, for example using screws.

The housing 120 encloses the disinfection chamber 110 therein. The disinfection chamber 110 is accessible for the disinfection target through the tunnel or other opening 121. In the present example, the tunnel 121 has a circular cross-section. The tunnel 121 may have a different shape. The opening 121 may have a width, in particular a diameter, of at least 5 mm, in particular at least 10 mm and/or at most 100 nm, in particular at most 40 mm.

The flashlamp, in particular the axis along the axial direction A of the flashtube 10, may be spaced apart vertically and/or radially with respect to the center of the target area defined by the opening or tunnel 121. The distance between the center of the opening or tunnel 121 in the vertical direction and/or a radial direction radial relative to a normal N defined by the target area can be at least 5 mm, in particular at least 10 mm, and/or at most 50 mm, in particular at most 30 mm. Alternatively, there may be an angular offset of at least 0°, at least 10°, at least 30°, and/or at most 90°, in particular at most 80° between the flashlamp, in particular the axis along the axial direction A of the flashtube, and the normal N through the center of the target area.

The decontamination unit 100 may include a radiation sensor 102 to detect ultraviolet radiation within the disinfection chamber 110. The sensor 102 may include the ability to measure the ultraviolet radiation and/or determine the magnitude of the radiation within the disinfection chamber 110 including a mechanism for comparing the magnitude of the radiation with a predetermined upper and/or lower threshold.

The housing 120 of the decontamination unit 100 and the flashlamp, in particular the flashlamp cartridge 1, may be formed correspondingly to one another such that the decontamination unit 100 may include one or more receivers for one or more flashlamps. The receivers may be realized for example as one or more slots 114, 115 extending from the outside surface 122 or 123 to an inside surface 112 and/or 113 defining the disinfection chamber 110. In particular, the one or more slots 114, 115 may be designed corresponding to the flashtube 10, in particular the flashlamp cartridge 1, such that at least sectionally, in particular completely, along the receiver, a positive connection is formed between the housing 120 and the flashlamp, particularly the flashlamp cartridge 1.

The first slot 114 may be equipped with one or more mounting features to engage corresponding mounting features of the flashlamp, particularly the flashlamp cartridge 1, in particular the radial nose 31 of the flashlamp cartridge 1, or the like. The slot 114, 115 or other receiver may have a cross-sectional width, for example a circular cross-section of a predetermined diameter, corresponding to the dimensions of the flashlamp, and particularly the flashlamp cartridge 1. The mounting features of the flashlamp, particularly the flashlamp cartridge 1, may determine the orientation of the flashlamp relative to the housing 120 and the target area, such that the flashlamp may irradiate the target area. To this end, one or more mounting features may define the orientation of the window 27 of the flashlamp cartridge 1 such that ultraviolet radiation emitted by the flashlamp is directed towards the disinfection target area. The extension of the disinfection chamber 110 in the axial direction A may be larger than or equal to the axial extension of the window 27. The decontamination unit 100 may comprise a mechanical and/or thermal manipulation tool to manipulate the target within the disinfection chamber 110.

In order to firmly attach the flashlamp, which may be integrated as the flashtube 10 within the flashlamp cartridge 1 to the housing 120 of the decontamination unit 100, one or more sockets 124, 125 may be provided with a respective interface 140, 150. The interface 140, 150 may correspond to exactly one or at least one port 40 or 50 of the flashlamp cartridge 1. The socket 124, 125 may include one or more mounting features 134, 135 to cooperate with one or more corresponding mounting features 34, 35 of the flashlamp cartridge 1. The interface 140, 150 of the socket 124, 125 may include media connectors 141, 143, 151, 152, 154 corresponding in shape and function to the media connectors of the flashlamp cartridge 1.

Figure 6:
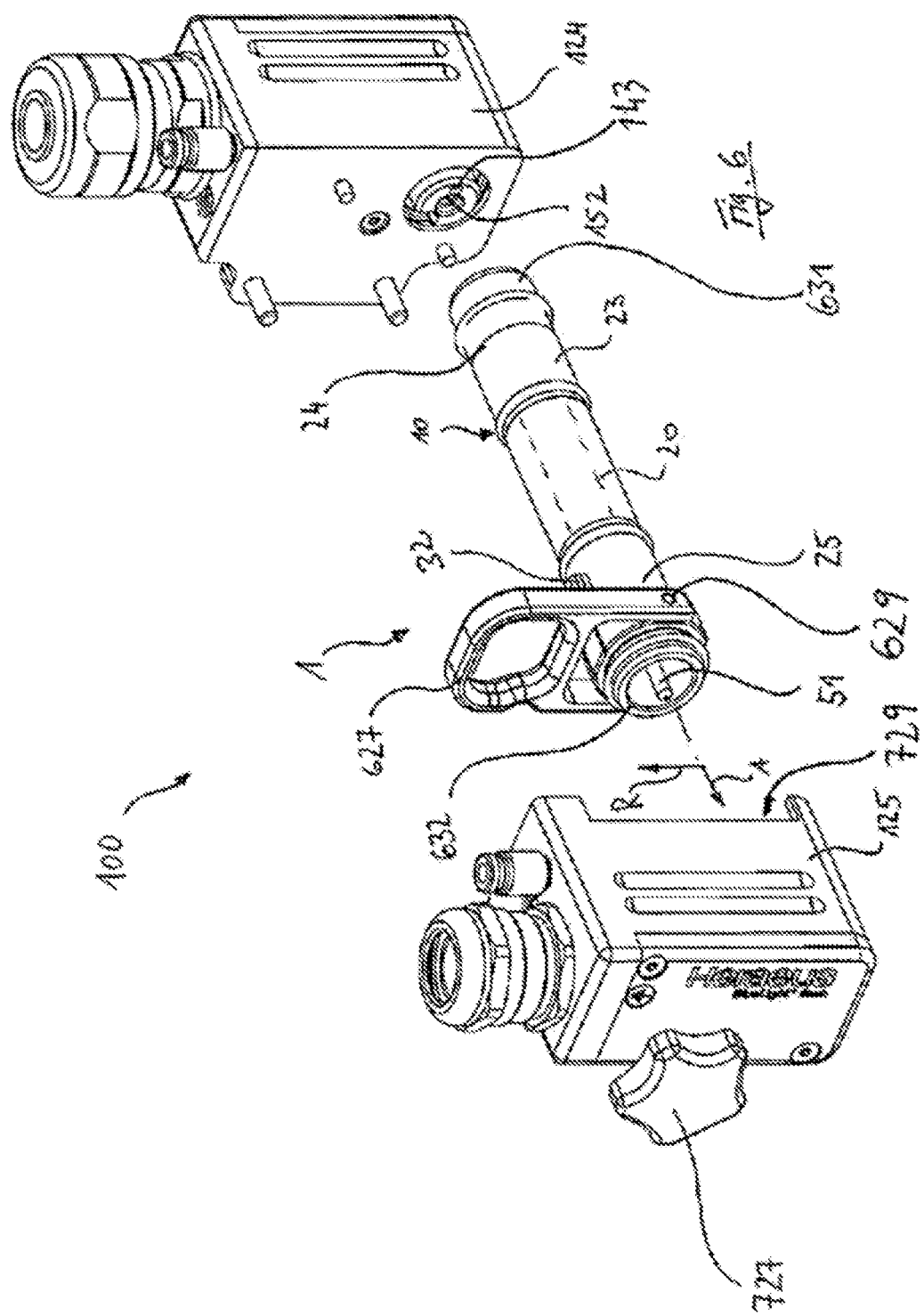
FIG. 6 shows an exploded view of a further embodiment of a flashlamp cartridge according to the invention between two sockets.

FIG. 6 shows a schematic illustration of a further flashlamp cartridge 1 within a partially shown decontamination unit 100. In a similar manner as in FIG. 3, the schematic drawing does not specifically show the housing 120, the features of which can be inferred from FIGS. 4A through 5B. The flashlamp cartridge 1 of FIG. 6 and the sockets 124, 125 in the embodiment shown in FIG. 6 are essentially identical to those previously described.

The flashlamp cartridge 1 of FIG. 6 differs from the aforementioned ones essentially only in the axially protruding, annular mounting features 631, 632 and the mounting tab 627. The sockets 124, 125 in the embodiment of FIG. 6 are adapted in accordance with the mounting features 631, 632 and the mounting tab 627. Furthermore, one of the sockets 125 includes a receiver 729 for receiving the mounting tab 627 of the flashlamp cartridge 1 when installed in the decontamination unit 100.

Furthermore, the socket 124 comprises a mounting or assembly screw 727 with an enlarged star-shaped screwhead for tool-free manual manipulation. The socket 125 can easily be disassembled from the housing 120 (not shown in further detail) using the assembly screw 727 without any tool for accelerated access to the flashlamp cartridge 1 and the slot 115 in the housing 120 for receiving the flashlamp cartridge 1. Instead of the shown assembly screw 727, another tool-free manually operable fixation device could alternatively be used, such as, for example a spring-biased bayonet latch or a quick-release skewer.

The flashlamp cartridge 1 has annular, axially protruding mounting features 631, 632 on each of its respective caps 24, 25 for engaging into complementarily shaped recesses in one of the sockets 124, 125, each. The annularly protruding mounting feature 632 extends further in the axial direction A than the media connectors of the flashlamp cartridge 1, for example the electrode connector 51. The media connectors, including the electrode connector 51, are protected by the sleeve-like annularly protruding mounting feature 632 (or 631). The annularly protruding mounting feature 631, 632 radially surrounds all media connectors on the respective cap 24 or 25 of the flashlamp cartridge 1.

The first cap 24 includes a radially inward protruding mounting feature (not shown in further detail) for connection with a respective complementarily shaped radial recess in the socket 124. The cap 25 is provided with a radially outwardly protruding mounting feature 32 for insertion into a complementarily shaped recess in the second socket 125 (not shown).

For ease of assembly and disassembly of the flashlamp cartridge 1 within the decontamination unit 100, the flashlamp cartridge 1 is provided with the mounting tab 627 which protrudes from the flashlamp cartridge 1 so as to form an outwardly extending bracket which a manual operator can easily grip in order to apply a pushing or pulling force in the axial direction A to mount or dismount the flashlamp cartridge 1. The mounting bracket or tab 627 can be attached rigidly to the flashlamp cartridge 1 or via a hinge connection 629. The hinge connection 629 allows for the mounting tab 627 to be oriented in a radially extending position for arrangement within the receiver 729 of the socket 125 when the flashlamp cartridge 1 is mounted in the decontamination unit 100. The mounting tab 627 can be moved via the hinged connection 629 to extend in the axial direction A from the cap 25 so that the manual operator may easily push the flashlamp cartridge 1 into the slot 115 and/or to pull the flashlamp cartridge 1 out of the slot 115 in the axial direction A.

The features disclosed in the specification and the drawings may be essential for different embodiments of the claimed invention, both separately and in any combination with each other.

EXAMPLES

The following examples are included to more clearly demonstrate the overall nature of the disclosure. These examples are exemplary, not restrictive, of the disclosure. Unless otherwise stated, it may be assumed that tests were conducted at an ambient temperature of 23° C., and ambient air pressure of 100 kPa (0.986 atm), and a relative humidity of 50%.

The following tests were conducted to establish the efficiency of the decontamination treatment using a flashlamp according to the invention. All tests for both *aspergillus brasiliensis* and *bacillus atrophaeus* exceeded a logarithmic reduction of 3.

TABLE 1

| Sample Description | PET-Film, 10.0 × 10.0 cm | |
|---|---|---|
| Inoculated Surface | 1.0 × 6.0 cm rectangle | |
| Microorganism | Aspergillus brasiliensis | DSM 1988 |
| Inoculation | Spray | |
| Initial Cell Count | 1.00E+06 | CFU/Object |
| Power | 800, 850, 900, 1000 V | |
| # of Flashes | 1 | |
| Distance | 10, 20, 30 mm | |

| Power V | Distance (x) cm | Flashes | mean CFU/object | mean log-red | Intensity $J/cm^2$ |
|---|---|---|---|---|---|
| 800 | 3 | 1 | 5.77E+01 | 4 | 0.559 |
| 900 | 3 | 1 | 1.17E+01 | 4.6 | 0.709 |
| 900 | 2 | 1 | 5.53E+01 | 4 | 1.01 |
| 850 | 2 | 1 | 2.10E+02 | 3.3 | 1.32 |
| 1000 | 1 | 1 | 1.57E+02 | 3.7 | 1.81 |

TABLE 2

| Sample Description | PET-Film, 10.0 × 10.0 cm | |
|---|---|---|
| Inoculated Surface | 1.0 × 6.0 cm rectangle | |
| Microorganism | Bacillus atrophaeus | DSM 675 |
| Inoculation | Spray | |
| Initial Cell Count | 1.00E+06 | CFU/Object |
| Power | 800, 850, 900, 1000 V | |
| # of Flashes | 1 | |
| Distance | 10, 20, 30 mm | |

| Power V | Distance (x) cm | Flashes | mean CFU/object | mean log-red | Intensity $J/cm^2$ |
|---|---|---|---|---|---|
| 800 | 3 | 1 | 2.80E+02 | 4.1 | 0.559 |
| 900 | 3 | 1 | 1.13E+02 | 4.6 | 0.709 |
| 900 | 2 | 1 | 9.07E+01 | 4.6 | 1.01 |
| 850 | 2 | 1 | 2.45E+02 | 4.4 | 1.32 |
| 1000 | 1 | 1 | 1.53E+02 | 4.4 | 1.81 |

Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure.

The invention claimed is:

1. A flashlamp cartridge for a decontamination unit, comprising:
    a flashtube for pulsed emissions of ultraviolet light,
    a sheath encapsulating the flashtube and extending axially from a first end, capped by a first cap, to a second end, capped by a second cap; and
    a coolant chamber extending radially between the flashtube and the sheath, wherein the coolant chamber extends axially from the first cap, which includes a first coolant connector as an inlet for coolant, to the second cap, which includes a second coolant connector as an outlet for the coolant.

2. The flashlamp cartridge of claim 1, wherein the sheath comprises at least one port comprising one or more media connectors extending through the sheath for supplying the flashtube.

3. The flashlamp cartridge of claim 2, further comprising two ports on different sides of the flashlamp cartridge, wherein the two ports are arranged on opposite ends of the flashlamp cartridge.

4. The flashlamp cartridge of claim 2, wherein the at least one port comprises at least one of the following media connectors: (i) an electrode connector, (ii) a trigger connector, (iii) a ground connector, and/or (iv) the first coolant connector or the second coolant connector.

5. The flashlamp cartridge of claim 1, wherein the sheath comprises an at least partially cylindrical tubular body surrounding the flashtube.

6. The flashlamp cartridge of claim 1, wherein the sheath comprises at least one mount for correct alignment and orientation of the flashlamp cartridge in a receiver.

7. A decontamination unit comprising:
a housing enclosing a disinfection chamber, defining an opening for insertion of a disinfection target into the disinfection chamber, and having an outside surface with a slot; and
a flashlamp cartridge configured to be received in the slot and comprising:
a flashtube for pulsed emissions of ultraviolet light, the flashtube being arranged in the housing to irradiate the disinfection target within the disinfection chamber, wherein the slot extends into the disinfection chamber and receives the flashlamp cartridge,
a sheath encapsulating the flashtube and extending axially from a first end, capped by a first cap, to a second end, capped by a second cap, and
a coolant chamber extending radially between the flashtube and the sheath, wherein the coolant chamber extends axially from the first cap, which includes a first coolant connector as an inlet for coolant, to the second cap, which includes a second coolant connector as an outlet for the coolant.

8. The decontamination unit of claim 7, further comprising at least one socket with an interface connected to the flashlamp cartridge and attached to the housing.

9. The decontamination unit of claim 8, wherein the at least one socket is attached to the outside surface of the housing, and/or wherein the at least one socket releasably attaches the flashlamp cartridge firmly to the housing.

10. The decontamination unit of claim 9, wherein the interface comprises a mount defining a predefined orientation and/or alignment of the flashlamp cartridge relative to the housing and/or wherein the interface contains at least one media connector for supplying the flashlamp cartridge, the at least one media connector comprising at least one of (i) an electrode connector, (ii) a trigger connector, (iii) a ground connector, and/or (iv) the first coolant connector or the second coolant connector.

11. The decontamination unit of claim 8, the decontamination unit further comprising a first socket and a second socket, wherein the first socket defines a first interface and the second socket defines a second interface different from the first interface, and wherein the first socket and the second socket comprise different mounts defining a predefined orientation and/or alignment of the flashlamp cartridge relative to the first and second sockets.

12. The decontamination unit of claim 7, the decontamination unit further comprising a first slot and a second slot, wherein the housing has different inside surfaces enclosing the disinfection chamber, wherein the first slot and the second slot pierce the different inside surfaces, and wherein the first slot and the second slot align.

13. The decontamination unit of claim 7, further comprising a sensor for detecting the ultraviolet light within the disinfection chamber.

14. The decontamination unit of claim 13, wherein the sensor measures the ultraviolet light and/or determines if the ultraviolet light exceeds a predetermined dosage threshold.

15. A decontamination unit comprising:
multiple decontamination units of claim 7; and
a controller operating the multiple decontamination units.

16. The decontamination unit of claim 15, further comprising a support structure carrying the decontamination units and an actuator causing the support structure to perform a repetitive motion.

17. The decontamination unit of claim 16, wherein the repetitive motion is a revolution or a linear back and forth movement.

18. The decontamination unit of claim 15, wherein the controller triggers individual flashlamp cartridges of the decontamination units at a frequency of less than 1 Hz, and/or wherein the controller triggers the individual flashlamp cartridges in a cascading manner.

19. The decontamination unit of claim 18, wherein the controller triggers individual flashlamp cartridges of the decontamination units at a frequency of approximately ⅓ Hz.

* * * * *